US011872149B2

United States Patent
Rodriguez et al.

(10) Patent No.: US 11,872,149 B2
(45) Date of Patent: *Jan. 16, 2024

(54) ENHANCED COMPRESSION SLEEVE FOR JOINTS

(71) Applicant: Brownmed, Inc., Boston, MA (US)

(72) Inventors: Brandon Rodriguez, Westwood, MA (US); Daniel Joseph Breton, Boston, MA (US); Tamara Gambardella, Kansas City, MO (US); Matt Garver, Boston, MA (US)

(73) Assignee: Brownmed, Inc., Boston, MA (US)

( * ) Notice: Subject to any disclaimer, the term of this patent is extended or adjusted under 35 U.S.C. 154(b) by 256 days.

This patent is subject to a terminal disclaimer.

(21) Appl. No.: 16/127,651

(22) Filed: Sep. 11, 2018

(65) Prior Publication Data

US 2020/0078201 A1  Mar. 12, 2020

(51) Int. Cl.
*A61F 5/01* (2006.01)
*A61F 13/08* (2006.01)

(52) U.S. Cl.
CPC .......... *A61F 5/0109* (2013.01); *A61F 13/08* (2013.01)

(58) Field of Classification Search
CPC ........ A61F 5/01–013; A61F 13/06–062; A61F 13/08–108; A61F 13/064–066; A61F 13/069–108; A61H 1/006; A61H 1/008
See application file for complete search history.

(56) References Cited

U.S. PATENT DOCUMENTS

| 2,589,241 | A | | 3/1952 | Galhouse et al. |
| 3,050,053 | A | | 8/1962 | Peckham |
| 3,805,781 | A | | 4/1974 | Hoey |
| 3,934,583 | A | | 1/1976 | Hollingshead et al. |
| 3,938,510 | A | | 2/1976 | Gerber |
| 5,676,641 | A | | 10/1997 | Arensdorf et al. |
| 5,938,631 | A | | 8/1999 | Colman |
| 6,048,326 | A | | 4/2000 | Davis et al. |
| 6,059,834 | A | * | 5/2000 | Springs ................. A61F 2/7812 623/32 |
| 6,063,048 | A | * | 5/2000 | Bodenschatz ......... A61F 13/061 2/24 |
| 6,315,748 | B1 | | 11/2001 | Morgan, Jr. |
| 6,641,550 | B1 | | 11/2003 | Johnson |
| 7,485,111 | B1 | * | 2/2009 | Choi .................... A61F 13/107 602/73 |
| 8,025,632 | B2 | * | 9/2011 | Einarsson ............. A61B 5/6812 602/26 |
| 8,523,793 | B1 | | 9/2013 | Waldon, Sr. |
| D758,598 | S | * | 6/2016 | Forbes ......................... D24/190 |
| 9,931,234 | B2 | * | 4/2018 | Gambardella ......... A61F 5/0127 |
| 2001/0007929 | A1 | * | 7/2001 | Schlomski ............. D04B 21/04 602/62 |

(Continued)

FOREIGN PATENT DOCUMENTS

JP  2001129015 A  5/2001
JP  2003268604 A  9/2003

*Primary Examiner* — Michelle J Lee
(74) *Attorney, Agent, or Firm* — McKee, Voorhees & Sease, PLC

(57) ABSTRACT

A flexible compressive orthopedic knee sleeve of stretchable fabric having an exterior surface webbing material at least partially covering the sleeve to provide targeted compressive force similar to athletic taping and to also provide kinetic retention.

7 Claims, 6 Drawing Sheets

(56) References Cited

U.S. PATENT DOCUMENTS

| | | | |
|---|---|---|---|
| 2001/0031936 A1* | 10/2001 | Pior | A61F 5/0111 |
| | | | 602/27 |
| 2003/0069530 A1 | 4/2003 | Satou et al. | |
| 2005/0015037 A1 | 1/2005 | Dohira et al. | |
| 2005/0101693 A1 | 5/2005 | Arbogast et al. | |
| 2006/0030804 A1* | 2/2006 | Nordt, III | A61F 5/0106 |
| | | | 602/26 |
| 2006/0030806 A1* | 2/2006 | Nordt. III | A61F 5/0106 |
| | | | 602/26 |
| 2007/0021699 A1* | 1/2007 | Braunstein | A61F 5/0109 |
| | | | 602/5 |
| 2008/0139982 A1* | 6/2008 | Magnusson | A61F 13/061 |
| | | | 602/5 |
| 2010/0294814 A1* | 11/2010 | Geiwald | A41D 27/245 |
| | | | 223/3 |
| 2011/0082403 A1 | 4/2011 | Hill | |
| 2012/0136293 A1 | 5/2012 | Oosawa | |
| 2014/0058311 A1 | 2/2014 | Higgins | |
| 2014/0276321 A1 | 9/2014 | Sellitto | |
| 2014/0303534 A1* | 10/2014 | Huffa | A61F 5/0102 |
| | | | 602/6 |
| 2015/0119781 A1 | 4/2015 | Ponce | |
| 2016/0059516 A1* | 3/2016 | Harris | A61F 13/08 |
| | | | 442/1 |
| 2016/0081836 A1 | 3/2016 | Sawle et al. | |
| 2016/0100973 A1 | 4/2016 | Nelson | |
| 2016/0242946 A1* | 8/2016 | Gambardella | A61F 13/065 |

\* cited by examiner

ENHANCED COMPRESSION SLEEVE FOR JOINTS

FIELD OF THE INVENTION

This invention, in a preferred form relates to a knee support, specifically an orthopedic compression sleeve with improved performance characteristics particularly to enhance kinetic retention properties.

BACKGROUND OF THE INVENTION

The industry of pain relief has become a multi-million-dollar industry. Medicines and devices of all kinds are produced and marketed to relieve pain and to prevent further injury. As individual's get older, their bodies begin to break down and certain parts of their bodies tend to become prone to pain. Additionally, those individuals that are active may have injuries from over strenuous use of their bodies.

In particular, individuals like runners, jumpers and other athletes such as skiers, cyclists and soccer players put heavy stress on their knees. The muscles that surround the knee provide mobility and strength to the legs. When athletes run or jump, the kneecap alone often endures forces of 1000 to 1500 pounds. The entire knee joint is under massive stress with these kinds of activities, especially when there are imbalances in muscle strength or flexibility. In time, overuse injuries, such as tendonitis, chondromalacia, runner's and jumper's knee, iliotibial band syndrome and Osgood Schlatter's disease, may develop.

The knee joint includes the patella or kneecap which is a thick, triangular bone which articulates with the femur and covers and protects the front of the knee joint. It is attached to the tendon of the quadriceps femoris muscle, which contracts to straighten the leg. The primary functional role of the patella is knee extension. The patella increases the leverage that the tendon can exert on the femur by increasing the angle at which it acts. Injuries to the patella can be very painful.

To alleviate some of the pain, knee braces are often worn on the affected leg. Conventional knee braces are generally made of a sleeve of soft material, such as Neoprene, and often have a cutout for the patella. Furthermore, most conventional braces are 'static' where there is no actual force applied to the patella, although some conventional braces are 'dynamic' and have elasticized straps for creating dynamic, medially displacing force to the patella.

Knee braces and wraps and sleeves, of various types are known and vary widely from simple bandage wraps to complex devices for treatment of things such as restless leg syndrome. See, for example, U.S. Pat. No. 7,594,897 (commonly owned) for a knee support strap that fits below the patella, and U.S. 2009/02211943, a complex device stimulating mechanical vibration for restless leg syndrome; and finally, Walden, U.S. Pat. No. 8,523,793, Ser. No. 13/653, 241 filed Oct. 16, 2012, and issued Sep. 3, 2013. Walden is a strap on tapered knee brace with a patella cut out and vibrating motors spaced around the cutout; preferably it is made of neoprene.

Sleeves of various elasticity are known for use over and around the knee. Gambardella, U.S. Pat. No. 9,931,234 relates to a foot sleeve useful for plantar fasciitis. The theory is that they provide an inward compressive force to enhance holding the knee or other joints together. There is however continuing need to improve these devices, both from the standpoint of effective knee support and targeted enhanced compression in areas that are particularly in need of such targeted enhanced compression.

A still further need is a knee support that is simple and effective in construction, not cumbersome, mechanical in nature, and heavy.

Accordingly, it is a primary objective of the present invention to provide an enhanced compression sleeve having improved performance properties, in the sense that it has targeted compression where needed, is of simple construction and therefore economical, and uses enhanced compression construction to prevent lateral movement during a wearer's stretching and bending, while also kinetic retention and support.

A still further objective is to provide a sleeve which provides the benefits of a trainer's targeted taping without the need to utilize a trainer's services.

The method and manner of accomplishing each of the above objectives as well as other benefits of the invention will be apparent from the detailed description which follows.

SUMMARY OF THE INVENTION

A flexible compressive orthopedic knee sleeve of stretchable fabric having an exterior surface webbing material at least partially covering the sleeve to provide targeted compressive force similar to athletic taping and to also provide kinetic retention.

DETAILED DESCRIPTION OF THEE PREFERRED EMBODIMENTS

Figure 1:
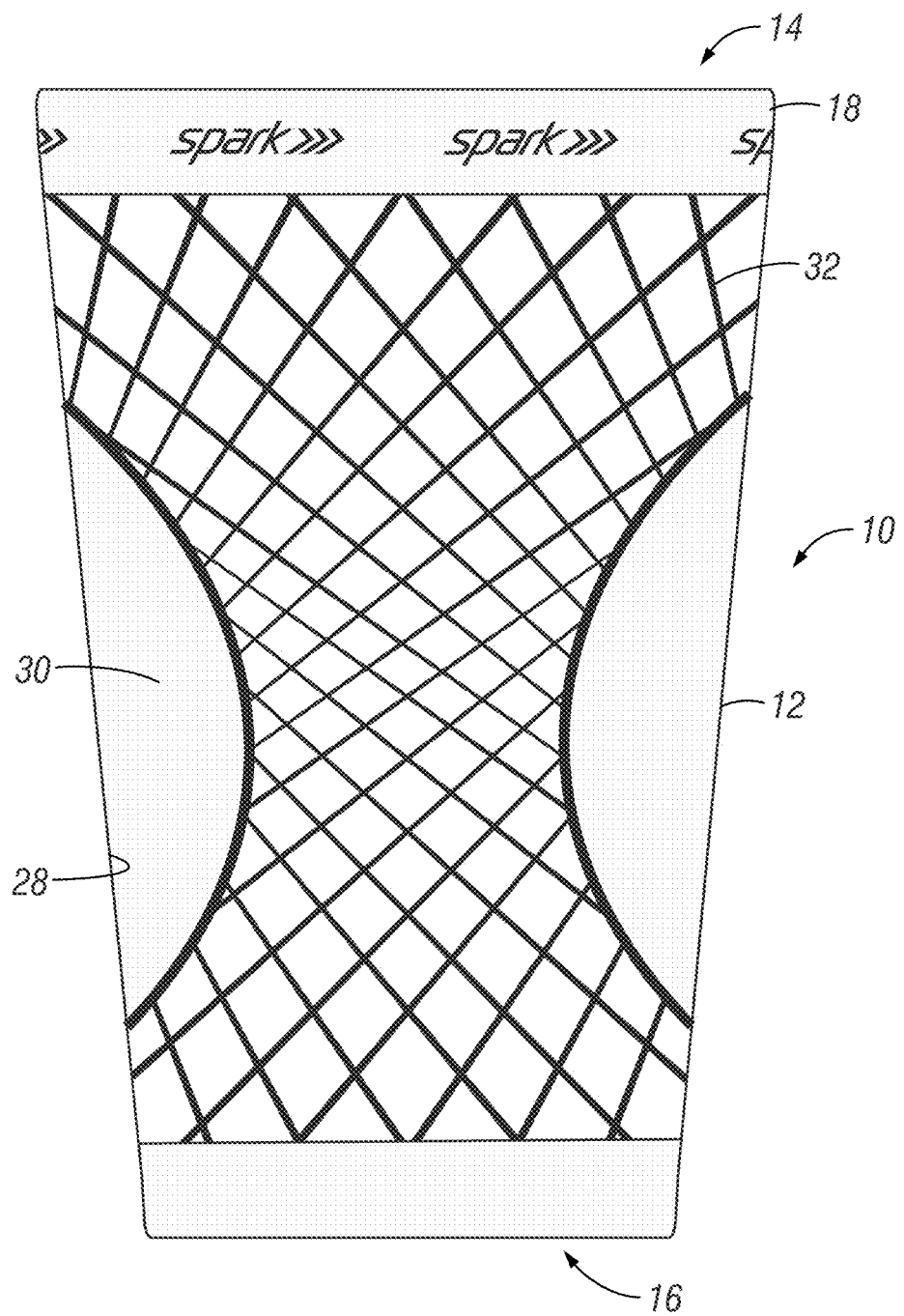
FIG. 1 is a front plan view of the compression sleeve of the present invention.
Figure 2:
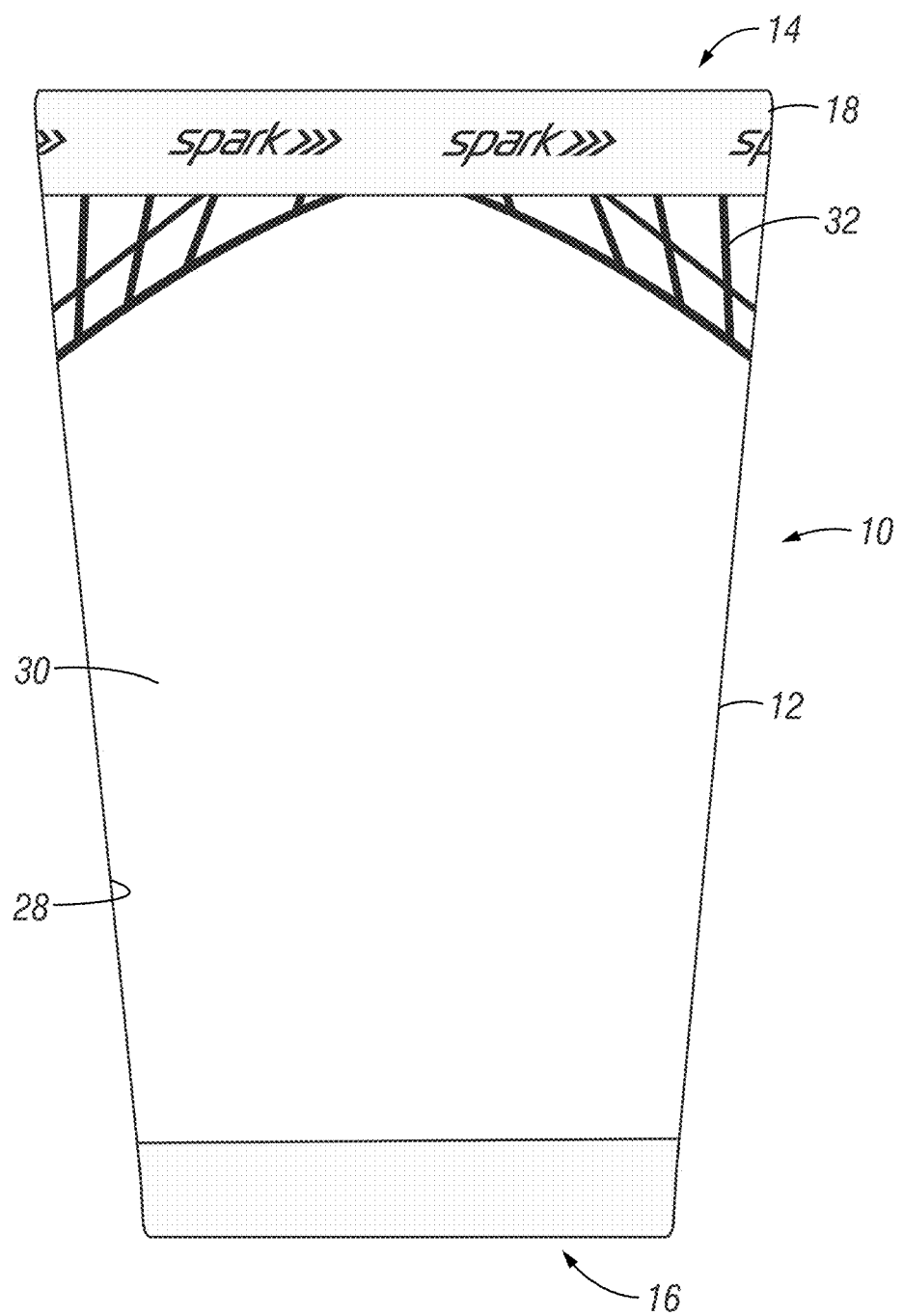
FIG. 2 is a back plan view of the compression sleeve of the present invention.
Figure 3:
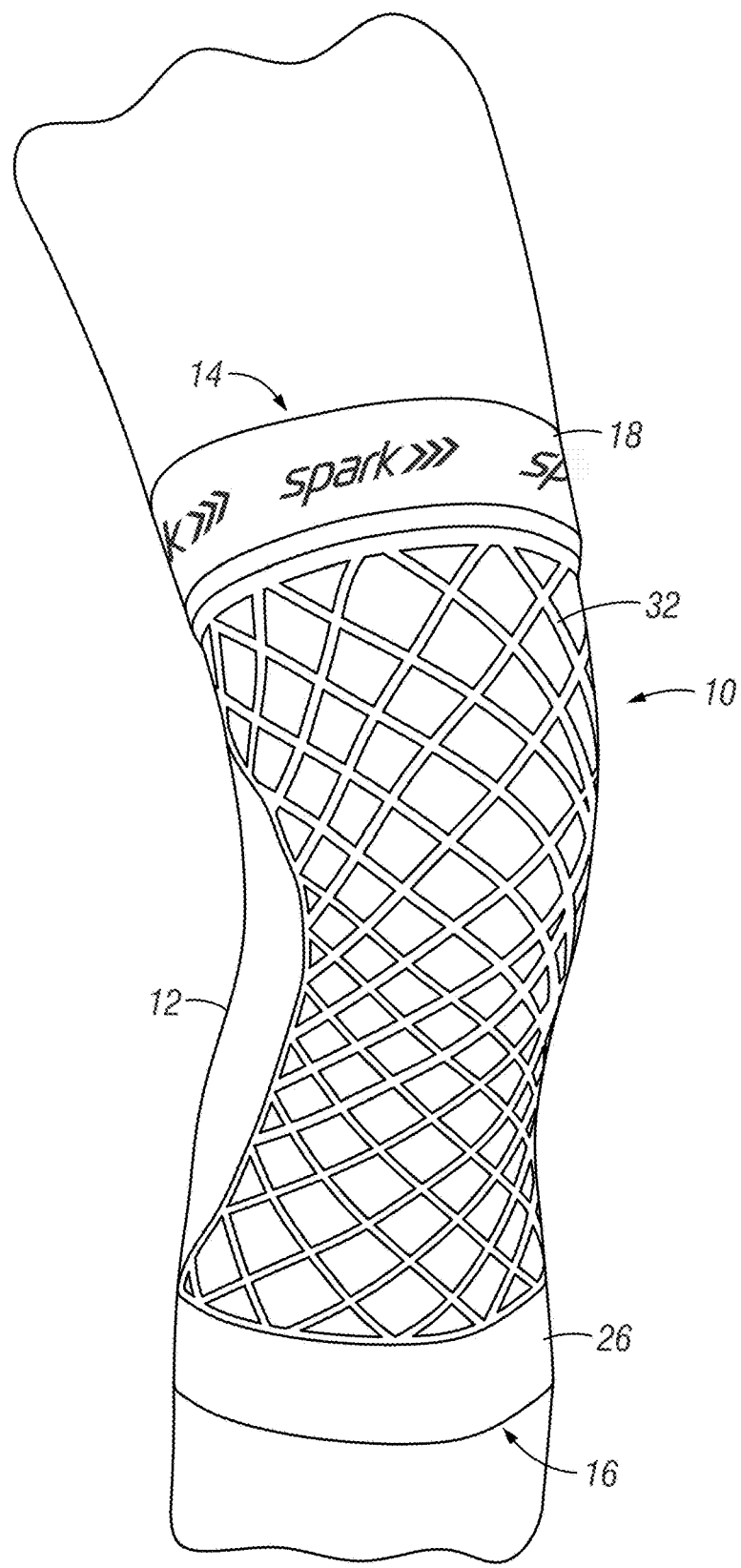
FIG. 3 is a perspective view of a person's lower leg and knee while wearing a compression sleeve of the present invention.
Figure 4A:
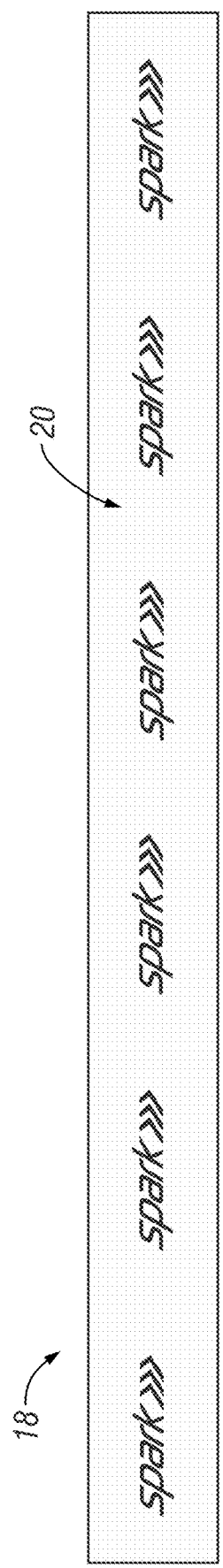
FIGS. 4 A and B show the grip silicone bonding which may be used along both the top and bottom opening, showing both the front and back side of the panel, front 4A, back 4B.
Figure 4B:
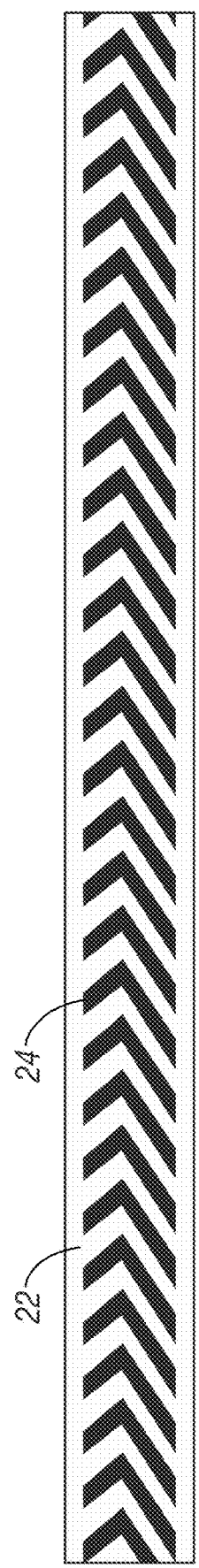
Figure 5:
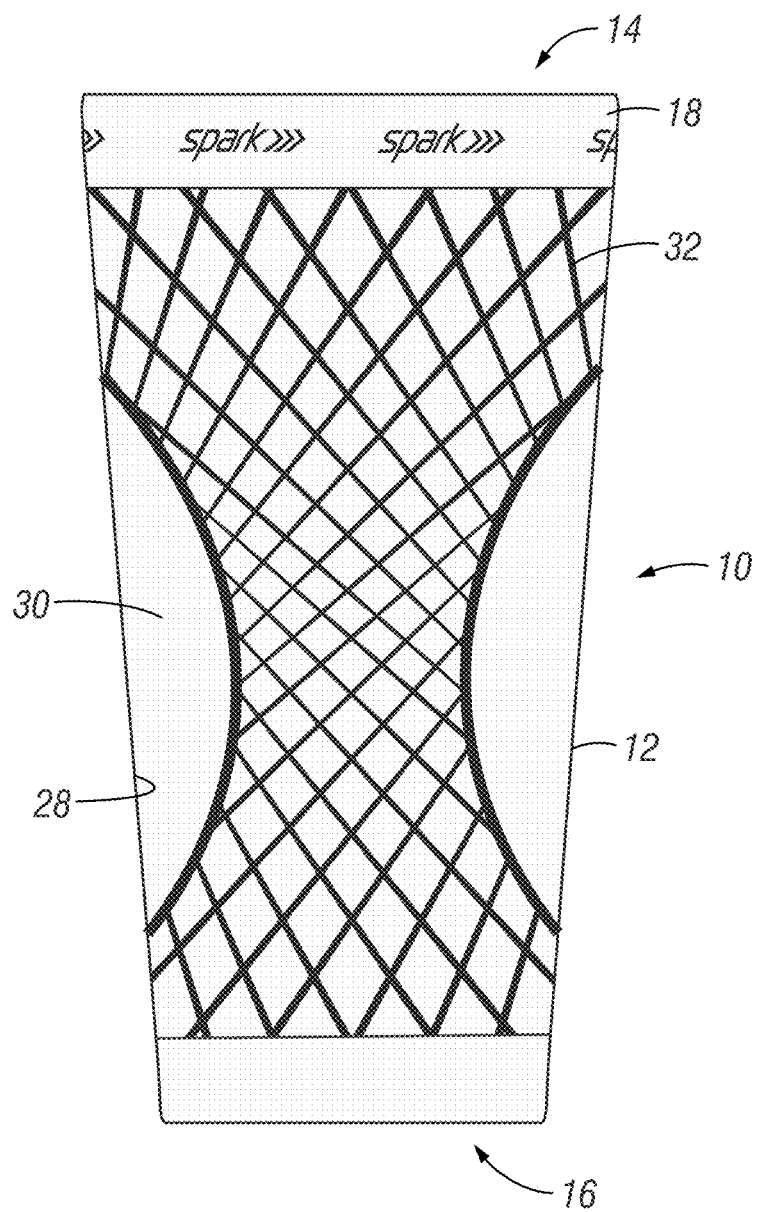
FIG. 5 is a plan view of an elbow compression sleeve of the invention.
Figure 6:
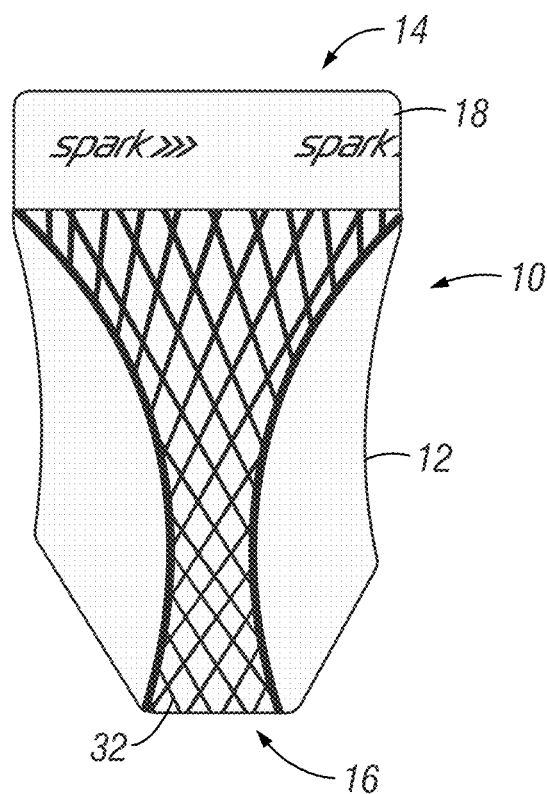
FIG. 6 is a plan view of an amble compression sleeve of the invention.

FIGS. 1-6 show preferred embodiments of the invention. Flexible compression knee sleeve 10 is generally comprised of a tubular compression material 12 having a top opening 14 and a bottom opening 16. The top opening 14 terminates in a top band 18 having an exterior surface 20 and an interior surface 22 (FIGS. 4A and 4B). Interior surface 22 of the top band 18 has a series of silicone grips 24 on the band interior surface 22. The silicone grips 24 prevent the slippage of the sleeve during use. While not shown because it is of identical construction, the bottom opening of the sleeve may have a bottom band 26 (see FIG. 3) or not of same construction of the top band 18. For some uses of a bottom band 26 is preferred in others it is not, depending upon the joint in question. The flexible compressive sleeve 10 has an interior surface 28 and exterior surface 30. As shown, the exterior surface 30 has at least a partial covering of attached polymeric webbing 32 of greater compressive force than the flexible compressive sleeve in order to reinforce compression orthopedically at strategic locations at or around the wearer's knee and to provide kinetic retention and support. This provides targeted reinforced compression similar to that of athletic tapes, without the need for additional taping.

High temperature polyurethane pressure sensitive adhesive tapes are known, see for example U.S. Pat. No. 3,756,848, patented Sep. 4, 1973 which is incorporated herein by reference. The polyurethane film applied this instance in the pattern of a webbing 32 disrupts the nature stretch of the elastic sleeve and promotes greater pill and compression in the targeted area. In this sense, it mimics taping methods typically recommended by professional trainers. The webbing 32 is a polymeric material selected from the group consisting of thermal polyurethane, polyurethane, thermal polyethylene, polyethylene, polyvinyl chloride, silicone, and neoprene. The material used for the webbing 32 is heat bonded to the stretchable compressive sleeve exterior 30 using known techniques. Suitable polyurethane tapes may be obtained from a variety of sources with one particularly suitable source being Framis Italia. S.p.A. of 20083 Vigano di Gaggiano M I, Italy. Framis Italia is a market leader in polyurethane heat bonding applications.

The webbing 32 may be heat bonded in a variety of different configurations depending upon kinesiology strategy employed. A particular, preferred configuration for knee reinforcement is shown in the drawings (particularly FIG. 3). As illustrated the weaker part of the knees are targeted for enhanced compression by the polymer web.

The preferred material for the compression sleeve itself is material that is part nylon and part lycra. Spandex® material may be employed. Such materials include generally thermal polyurethane, polyethylene, and polyvinyl chloride.

Worthy of note is the anchor system provided by the silicon grips 24 on the interior surface 22 of the top band 18 and if used the bottom band 26. It is designed so that one or both ends of the polymer film terminate at the elastic anchor system of the band which are designed to allow full stretch and fit with little location creep.

The sleeve 12 is made of a flat knit production to allow all width polymer film application of the webbing material 32. The sleeve may also have moisture wicking properties to reduce discomfort.

The compression sleeve 10 is reusable and machine washable without damage to any of the sleeve components.

While the compression sleeve has been described with most particularity with regard to the knee, it goes without need to express further that this same compression sleeve concept can be used for other joints such as hand, wrist, shin, ankle, elbow and the like. The important point being the combination of the orthopedic compression sleeve with a bonded webbing of different stronger compression force to provide kinetic retention and support throughout the sleeve and the underlying joints.

Having described the preferred embodiment, the invention is it can been seen at least accomplishes all of its stated objectives.

What is claimed is:

1. A flexible, compressive orthopedic sleeve of stretchable flat knit fabric having:
   a top opening and a bottom opening;
   at least said top opening having an attached perimeter band;
   said flexible compressive flat knit sleeve having an interior surface, and an exterior surface, and said exterior surface having a partial covering of attached polymeric webbing of greater compressive force than the flexible compressive flat knit sleeve to reinforce compression at orthopedic strategic locations wherein the polymeric webbing is heat bonded to the exterior surface of said flexible compressive flat knit sleeve to provide kinetic retention and support throughout the sleeve;
   wherein said polymeric webbing comprising interconnected film overlaid on the compressive flat knit sleeve in a pattern of a webbing, said pattern of the webbing covering less than a full area of the compressive flat knit sleeve and the less than full area being defined by opposite longitudinal edges extending from an upper, rear portion to a lower, front portion of the sleeve;
   said polymeric webbing being heat bonded to continuously overlie the flexible compressive flat knit sleeve between the opposite longitudinal edges which each form single, non-symmetrical catenary, and concave curves from the upper portion to the lower portion of the sleeve, wherein the single, non-symmetrical catenary, and concave curves face away from the polymeric webbing such that the longitudinal edges are only concave throughout the sleeve.

2. The flexible compressive orthopedic sleeve of claim 1 which has a perimeter band around the bottom opening.

3. The flexible compressive orthopedic sleeve of claim 1 wherein the attached and overlaid polymeric webbing is a polymeric material selected from the group consisting of thermal polyurethane, polyurethane, thermal polyethylene, polyethylene, polyvinyl chloride, silicone, and neoprene.

4. The flexible compressive orthopedic sleeve of claim 1 which includes silicone grips on an interior surface of the top attached perimeter band to minimize migration and shifting of the sleeve during use.

5. The flexible compressive orthopedic sleeve of claim 1 which includes silicone grips on any interior surface of any attached perimeter bands.

6. The flexible compressive orthopedic sleeve of claim 1 which includes at least one material to provide wicking properties to the sleeve.

7. The flexible compressive orthopedic sleeve of claim 1 wherein the sleeve is for a joint selected from hand, wrist, ankle, elbow and knee.

* * * * *